United States Patent
Rabizadeh et al.

(10) Patent No.: US 11,229,668 B2
(45) Date of Patent: Jan. 25, 2022

(54) MAXIMIZING T-CELL MEMORY AND COMPOSITIONS AND METHODS THEREFOR

(71) Applicants: NANTCELL, INC., Culver City, CA (US); NANT HOLDINGS IP, LLC, Culver City, CA (US)

(72) Inventors: Shahrooz Rabizadeh, Culver City, CA (US); Kayvan Niazi, Culver City, CA (US); Patrick Soon-Shiong, Culver City, CA (US); Hing Wong, Weston, FL (US); Wenxin Xu, Pembroke Pines, FL (US)

(73) Assignees: NantCell, Inc., Culver City, CA (US); Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 16/483,978

(22) PCT Filed: Feb. 8, 2018

(86) PCT No.: PCT/US2018/017383
§ 371 (c)(1),
(2) Date: Aug. 6, 2019

(87) PCT Pub. No.: WO2018/148381
PCT Pub. Date: Aug. 16, 2018

(65) Prior Publication Data
US 2020/0023008 A1   Jan. 23, 2020

Related U.S. Application Data

(60) Provisional application No. 62/455,999, filed on Feb. 7, 2017.

(51) Int. Cl.
| | | |
|---|---|---|
| *A61K 35/17* | (2015.01) | |
| *A61K 31/675* | (2006.01) | |
| *C07K 14/52* | (2006.01) | |
| *C12N 15/86* | (2006.01) | |

(52) U.S. Cl.
CPC ............ *A61K 35/17* (2013.01); *A61K 31/675* (2013.01); *C07K 14/521* (2013.01); *C12N 15/86* (2013.01)

(58) Field of Classification Search
CPC ...................................................... A61K 35/17
See application file for complete search history.

(56) References Cited

U.S. PATENT DOCUMENTS

| | | | |
|---|---|---|---|
| 5,811,097 A | 9/1998 | Allison et al. | |
| 5,855,887 A | 1/1999 | Allison et al. | |
| 6,051,227 A | 4/2000 | Allison et al. | |
| 6,984,720 B1 | 1/2006 | Korman et al. | |
| 7,758,891 B2 | 7/2010 | Desai et al. | |
| 7,771,751 B2 | 8/2010 | Desai et al. | |
| 7,780,984 B2 | 8/2010 | Desai et al. | |
| 7,981,445 B2 | 7/2011 | De et al. | |
| 8,034,375 B2 | 10/2011 | Desai et al. | |
| 2005/0201994 A1 | 9/2005 | Korman et al. | |
| 2006/0204509 A1 | 9/2006 | Harty et al. | |
| 2006/0263389 A1 | 11/2006 | Stacy et al. | |
| 2012/0059670 A1 | 3/2012 | Sanborn et al. | |
| 2012/0066001 A1 | 3/2012 | Sanborn et al. | |
| 2016/0030536 A1* | 2/2016 | Weiner ................... | A61P 35/02 424/85.2 |
| 2016/0058852 A1 | 3/2016 | Ter meulen et al. | |
| 2016/0206718 A1 | 7/2016 | Har-Noy | |

FOREIGN PATENT DOCUMENTS

| | | |
|---|---|---|
| CA | 3 052 803 A1 | 8/2018 |
| EP | 1 212 422 B1 | 2/2007 |
| EP | 2 532 740 A1 | 12/2012 |
| KR | 10-2016-0093012 A | 8/2016 |
| WO | 01/14424 A2 | 3/2001 |
| WO | 2004/035607 A3 | 8/2004 |
| WO | 2011/139345 A3 | 3/2012 |
| WO | 2013/062505 A1 | 5/2013 |
| WO | 2015/095811 A2 | 6/2015 |
| WO | 2016/123285 A1 | 8/2016 |
| WO | 2016/146035 A1 | 9/2016 |
| WO | 2016/161347 A1 | 10/2016 |
| WO | 2016/172249 A1 | 10/2016 |

(Continued)

OTHER PUBLICATIONS

Kim et al. (Immunological Investigations, 2014; 43(6): 517-534). (Year: 2014).*
Gabitzsch et al. (Cancer Immunol Immunother (2010) 59:1131-1135). (Year: 2010).*
Kim et al. (Oncotarget. Mar. 29, 2016;7(13):16130-45. doi: 10.18632/oncotarget.7470.) (Year: 2016).*
Office Action received for Canadian Application Serial No. CA3052803, dated Aug. 17, 2020, 5 pages.
International Preliminary Report on Patentability Chapter II recieved for PCT Application Serial No. PCT/US2018/017383 dated May 28, 2019, 7 pages.

(Continued)

*Primary Examiner* — Scott Long
(74) *Attorney, Agent, or Firm* — Martin Fessenmaier; Umberg Zipser LLP

(57) ABSTRACT

Contemplated treatments and methods produce substantially increased quantities of memory T-cells and a persistent immune response by subcutaneous and/or subdermal co-administration of (1) a vector comprising a recombinant nucleic acid that encodes a cancer associated epitope, a cancer specific epitope, and/or a neoepitope, (2) an immune stimulating cytokine, and (3) a checkpoint inhibitor. Most typically, the co-administration is performed at substantially the same location, preferably within 1-21 days from each other, and the vector is an adenoviral expression vector, for example, included in a viral particle such as an AdV5 virus with a deletion of the E2b gene.

20 Claims, No Drawings

(56) References Cited

FOREIGN PATENT DOCUMENTS

| WO | 2016/172722 A1 | 10/2016 |
| WO | 2017/222619 A2 | 12/2017 |
| WO | 2018/148381 A1 | 8/2018 |

OTHER PUBLICATIONS

Bassani-Sternberg, Michal et al., "Direct identification of clinically relevant neoepitopes presented on native human melanoma tissue by mass spectrometry", Nature Communications, Nov. 21, 2016, vol. 7, Article No. 13404, internal pp. 1-16.

International Search Report and Written Opinion received for PCT Application Serial No. PCT/US2018/017383 dated May 31, 2018, 16 pages.

Lee et al., "In-situ diversification of immunity following vaccination targeting tumor neoepitopes; an integral component of combinational immunotherapy", Cancer Immunology Research, May 2019, 47 pages.

Morvan et al., "NK cells and cancer: you can teach innate cells new tricks", Nature Reviews, Jan. 2016, vol. 16, 13 pages.

Qiu et al., 'Reviving virus based cancer vaccines by using cytomegalovirus vectors expressing modified tumor antigens', OncoImmunology, Jan. 2016, vol. 5, No. 1, 4 pages.

T.Weed et al., "Tadalafil Reduces Myeloid-Derived Suppressor Cells and Regulatory T Cells and Promotes Tumor Immunity in Patients with Head and Neck Squamous Cell Carcinoma", Clinical Cancer Research, Jan. 1, 2015, vol. 21, No. 1, 11 pages.

Topfer et al., "Tumor Evasion from T Cell Surveillance", Journal of Biomedicine and Biotechnology, 2011, vol. 2011, 20 pages.

Thakur et al., "Immunotherapy and Immune Evasion in Prostate Cancer", Cancers, 2013, vol. 5, pp. 569-590.

Extended European Search Report received for European Patent Application Serial No. 18751027.6 dated Nov. 12, 2020, 7 pages.

Amalfitano et al., "Production and Characterization of Improved Adenovirus Vectors with the E1, E2b, and E3 Genes Deleted", Journal of Virology, Feb. 1998, vol. 72, No. 2, pp. 926-933.

Niazi et al., "Activation of human CD4+T cells by targeting MHC class II epitopes to endosomal compartments using human CD1 tail sequences", Immunology, 2007, vol. 122, No. 4, pp. 522-531.

Brignone et al., "A Soluble Form of Lymphocyte Activation Gene-3 (IMP321) Induces Activation of a Large Range of Human Effector Cytotoxic Cells", The Journal of Immunology, 2007, vol. 179, No. 6, pp. 4202-4211.

Loo et al., "Development of an Fc-Enhanced Anti-B7-H3 Monoclonal Antibody with Potent Antitumor Activity", Clinical Cancer Research, 2012, vol. 18, No. 14, pp. 3834-3845.

Fourcade et al., "Upregulation of Tim-3 and PD-1 expression is associated with tumor antigen-specific CD8+T cell dysfunction in melanoma patients", The Journal of Experimental Medicine, 2010, vol. 207, No. 10, pp. 2175-2186.

Sakuishi et al., "Targeting Tim-3 and PD-1 pathways to reverse T cell exhaustion and restore anti-tumor immunity", The Journal of Experimental Medicine, 2010, vol. 207, No. 10, pp. 2187-2194.

Han et al., "IL-15:IL-15 receptor alpha superagonist complex: High-level co-expression in recombinant mammalian cells, purification and characterization", Cytokine, 2011, vol. 56, No. 3, pp. 804-810.

Wong et al., "The IL-15-based superagonist ALT-803 promotes the antigen-independent conversion of memory CD8+T cells into innate-like effector cells with antitumor activity", OncoImmunology, 2013, vol. 2, No. 11, e26442, 4 pages.

Morvan et al., "NK cells and cancer: you can teach innate cells new tricks", Nature Reviews Cancer, Jan. 2016, vol. 16, pp. 7-19.

First Examination Report received for Australian Application Serial No. AU2018219862, dated Jun. 19, 2020, 7 pages.

Second Examination Report received for Australian Application Serial No. AU2018219862, dated Aug. 12, 2020, 3 pages.

Miller et al., "First-in-human' phase I dose escalation trial of IL-15N72D/IL-15Rα-Fc superagonist complex (ALT-803) demonstrates immune activation with anti-tumor activity in patients with relapsed hematological malignancy", Blood, 2915, vol. 126, No. 23, pp. 1957.

Notice of acceptance received for Australian Application Serial No. AU2018219862, dated Aug. 28, 2020, 3 pages.

Office Action received for Canadian Patent Application Serial No. 3052803, dated Aug. 19, 2021, 3 pages.

\* cited by examiner

MAXIMIZING T-CELL MEMORY AND COMPOSITIONS AND METHODS THEREFOR

This application claims priority to our U.S. provisional application with the Ser. No. 62/455,999, which was filed Feb. 7, 2017.

FIELD OF THE INVENTION

The field of the invention is immunotherapy, especially as it relates to immunotherapy of cancer.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Immunotherapy of cancer has become an increasingly promising avenue in the treatment of cancer, but has also revealed the complexity of generating an immune response to a diseased tissue that is immunologically derived from a healthy tissue. These difficulties are compounded by the relatively low frequency of immunogenic cancer neoepitopes, insufficient co-stimulation, and inhibitory molecules produced by many cancer cells.

T-cells were shown to play an important role in controlling the development of neoplastic lesions in vivo. T-cells are activated via their T-cell receptor that binds to short antigen peptides presented on major histocompatibility complex class molecules (MHCs). Upon recognition of peptides presented by the MHC I complex, CD8+ cytotoxic T-cells (CTLs) are activated and can destroy target cells presenting the peptides using certain ligands (e.g., via TRAIL, TNF-related apoptosis-inducing ligand) or via lysis using perforin/granzyme. In addition, CD4+ T-cells recognize foreign or disease-associated peptides presented by the MHCII complex and improve the capacity of dendritic cells (DCs) to induce CTLs by crosslinking the co-stimulatory molecule CD40 on DCs with the CD40 ligand on activated CD4+ T-cells. Furthermore, by secreting cytokines such as interleukin-2 (IL-2), activated CD4+ T-cells support the clonal expansion of activated CTLs. Besides this, activated CD4+ T-cells can significantly boost cellular components of the innate immunity, such as macrophages and NK cells by enhanced IFN-γ secretion. Concomitantly, increased IFN-γ levels improve the recognition capacity of T-cells through induction of higher expression levels of MHCI molecules on the target cells.

Unfortunately, these processes can be modulated by cancer cells, and it has been shown that some cancer cells have evaded immune recognition by loss or downregulation of TAP and MHC components, and apoptosis mediators, or by various metabolic mechanism (e.g., arginine or tryptophan depletion). In still other cases, tumors have expressed increased quantities of cytokines (e.g., IL-10, TGF-beta) or other regulator factors (e.g., MIF), and especially factors for T-cells (e.g., Fas-ligand, PD-L1, MICA). In addition, Tregs (regulatory T-cells, or suppressor T-cells, many of which are CTLA-4 positive) can accumulate at a tumor site, leading to additional immune evasion. Clearly, a single pharmaceutical intervention will fail to address the multiple facets associated with immune evasion of tumor cells. Moreover, even if an immune response is at least somewhat effective, suitable memory T-cell generation to produce a therapeutic and durable response is not always achieved.

More recently, attempts have been undertaken to increase memory T cells in a patient by ex vivo cultivating the patients T cells in the presence of an antigen and subsequent isolation of T cells that secrete interferon gamma. Such isolated cells were then further propagated in the presence of IL-2 and IL-7, and either an inhibitor of the mTOR complex or an inhibitor of the IL2/IL2-receptor interaction as described in EP 2532740. However, such approach is relatively complex and requires numerous steps in the preparation of suitable cells. In yet another approach, as described in US 2006/0204509, peptide coated dendritic cells lead to large numbers of CD8+ T cells with the phenotype and function of memory T cells. While large numbers of such cells could be produced, concurrent inflammation often reduces rapid generation of memory T cells in the context of dendritic cell immunization.

In certain combination therapies, antigens and checkpoint inhibitors were used to enhance an immune response to selected antigens (e.g., HPV, HIV, HBV, HCV, etc.) as disclosed in WO2016/123285. Similarly, use of a cell based therapy with activated T cells or PBMCs is described in WO 2016/146035 for antitumor therapy. In still further known methods, a viral vector for expression of an antigen was used in combination with a checkpoint inhibitor to enhance immune response as described in WO2016/172249. While such combination appeared to increase CD8+ T cell responses, they did not appear to stimulate memory T cell formation. Increased memory formation was reported in WO 2016/161347. Here, checkpoint inhibitors were combined with a Bruton's typrosine kinase (Btk) inhibitor. However, Btk inhibitors may not be well tolerated and the combination of the Btk and checkpoint inhibitor may lead to an uncoordinated overreaction (cytokine storm) of the immune system.

Therefore, there is still a need for improved treatment systems and methods to increase efficacy of immunotherapy and to improve memory T-cell formation.

SUMMARY OF THE INVENTION

The inventor has now discovered that multiple factors and treatment modalities in cancer immune therapy can be combined (preferably in a synergistic manner) to substantially improve efficacy of immunotherapy and memory T-cell formation in a patient. For example, various immune evading strategies by a tumor can be effectively addressed by stimulating T-cell responses with adenoviral or yeast vector vaccines using one or more cancer associated epitopes, cancer specific epitopes, and/or neoepitopes, administration of IL-15 (or IL-15 analogs) and a checkpoint inhibitor, typically by subcutaneous or subdermal injection. Moreover, traditional treatment may further enhance immune mediated cancer clearance by administration of activated NK cells, with low-dose chemotherapy and/or radiation, and/or drugs that reduce production or activity of Tregs, M2 macrophages and/or myleoid derived suppressor cells.

In one aspect of the inventive subject matter, the inventor contemplates a method of stimulating development of memory T-cells against a cancer associated epitope, a cancer specific epitope, and/or a neoepitope in a patient that includes a step of co-administering by subcutaneous or subdermal injection (1) vector with a recombinant nucleic acid that encodes the cancer associated epitope, the cancer specific epitope, and/or the neoepitope; (2) an immune stimulating cytokine; and (3) a checkpoint inhibitor. In preferred methods, the step of co-administering is performed under a protocol such that the vector, the cytokine, and the checkpoint inhibitor are present in measurable quantities at the same time. Moreover, where desired, the vector is co-administered via a viral particle (e.g., adenovirus).

Additionally, or alternatively, it is contemplated that the method may include a further step of administering low-dose chemotherapy and/or radiation under a protocol effective to stimulate overexpression of the cancer associated epitope, the cancer specific epitope, the neoepitope, and/or a NKG2D ligand, or a further step of administering a drug that reduces number or function of Tregs (e.g., cyclophosphamide), M2 macrophages (e.g. nab-paclitaxel) and/or myleoid derived suppressor cells (e.g., gemcitabine or a phosphodiesterase-5 (PDE5) inhibitor). Furthermore, contemplated methods may include an additional step of administering a drug that increases T-cells when given metronomically in low doses (e.g., cyclophosphamide or 5-fluorouracil), or a step of administering a chemokine and/or a cell-based composition comprising an immune competent cell (e.g., T-cell, optionally having a chimeric antigen receptor, or a NK cell, optionally having a high-affinity CD16 or a chimeric antigen receptor).

It is still further contemplated that the recombinant nucleic acid further encodes a cytokine, a co-stimulatory molecule, and/or a checkpoint inhibitor, in which case the cytokine and/or the checkpoint inhibitor encoded in the recombinant nucleic acid may replace at least in part the subcutaneously or subdermally injected cytokine or checkpoint inhibitor. While not limiting the inventive subject matter, it is further contemplated that the vector, the cytokine, and the checkpoint inhibitor are injected at substantially the same site within 7-21 days, or within 2-14 days, or within one day.

In another aspect of the inventive subject matter, the inventor also contemplates a method of eliciting a durable immune response against a tumor expressing at least one of a cancer associated epitope, a cancer specific epitope, and a neoepitope in a patient. Such methods will include a step of co-administering by subcutaneous or subdermal injection (1) a vector with recombinant nucleic acid that encodes the cancer associated epitope, the cancer specific epitope, and/or the neoepitope; (2) an immune stimulating cytokine; and (3) at least one checkpoint inhibitor, wherein co-administering is performed under a protocol effective to trigger formation or propagation of memory T-cells in an amount sufficient to produce a persistent immune response against the tumor.

Where desired or needed, the method may further include at least one additional step, including (1) administering low-dose chemotherapy and/or radiation under a protocol effective to stimulate overexpression of the cancer associated epitope, the cancer specific epitope, the neoepitope, and/or a NKG2D ligand; (2) administering a drug that reduces number or function of Tregs, M2 macrophages and/or myleoid derived suppressor cells; (3) administering a drug that increases T-cells when given metronomically in low doses; (4) administering a chemokine; and (5) administering a cell-based composition comprising an immune competent cell. Most typically, and as noted above, the vector, the cytokine, and the checkpoint inhibitor are injected at substantially the same site within 1-21 days.

Therefore, and viewed from a different perspective, the inventor also contemplates use of (1) a vector with recombinant nucleic acid that encodes a cancer associated epitope, a cancer specific epitope, and/or a neoepitope, (2) an immune stimulating cytokine, and (3) a checkpoint inhibitor to increase memory T-cell formation in a patient. Where desired, the vector may be replaced with a peptide that is a cancer associated epitope, a cancer specific epitope, or a neoepitope, and it is further preferred that the vector, the cytokine, and the checkpoint inhibitor are formulated for subcutaneous or subdermal injection.

Various objects, features, aspects and advantages of the inventive subject matter will become more apparent from the following detailed description of preferred embodiments, along with the accompanying drawing figures in which like numerals represent like components.

DETAILED DESCRIPTION

The inventive subject matter is drawn to various compositions and methods of improving immunotherapy in a patient. More specifically, the inventor has discovered that immune evasion by a tumor can be reverted or at least partially broken by addressing multiple pathways critical to a therapeutically effective and durable immune response.

To that end, in one contemplated aspect of the inventive subject matter, an additive or even synergistic combination of therapeutic interventions is provided that (1) trains cellular immune response to tumor associated epitopes and/or patient specific tumor neoepitopes to so develop a T cell/NK cell response, (2) targets tumor associated epitopes and/or patient specific tumor neoepitopes using antibodies and optionally activated NK cells to so facilitate a rapid NK response against surface bound epitopes, (3) employs a low-dose and preferably metronomic chemotherapy that leads to presentation of stress signals effective to facilitate NK-cell based cell lysis or apoptosis, which in turn exposes intracellular epitopes, and (4) reduces activity of various suppressor cells and/or immune suppressive mechanisms via chemotherapy and/or administration of checkpoint inhibitors. Such specific and extended intervention is especially contemplated to maximize formation of a persistent immune response along with increased memory T cell formation (as compared to any single treatment regimen, for example, using checkpoint inhibition, chemotherapy, or antigen exposure). Viewed from another perspective, coordinated and patient specific treatment is expected to significantly increase therapeutic efficacy. Moreover, it should also be appreciated that contemplated treatment methods may be iteratively provided to the patient, with each round of treatment relying on a new determination of tumor associated epitopes and/or patient specific tumor neoepitopes to build an ever increasing immunity against the tumor.

For example, in a further aspect and with regard to preferred routes of administration, it is contemplated that immunity, T cell activation and memory T cell formation with respect to cancer associated epitopes, cancer specific epitopes, and/or neoepitope cancer is increased by subcutaneous or subdermal injection of at least a combination of (1) a recombinant vector, and most preferably an adenoviral expression vector delivered as a viral particle, that includes a nucleic acid segment that encodes the cancer associated epitope, the cancer specific epitope, and/or the neoepitope, (2) an immune stimulating cytokine or analog thereof, (3) a checkpoint inhibitor or other drug that reduces immune suppression or suppressor cells, and possibly (4) an activated NK cell, optionally genetically modified and most preferably in association with an antibody. Additionally, as noted earlier, the patient may still further undergo radiation or low-dose chemotherapy to stress tumor cells, thereby further triggering NK cell responses.

Most typically, administration is performed under a protocol such that the vector, the cytokine, and the checkpoint inhibitor are present in measurable quantities at the same time. For example, the vector or recombinant virus containing the vector may be subcutaneously or subdermally injected in a first administration, while the cytokine and the checkpoint inhibitor are separately co-administered in a second administration. Alternatively, all components may also be injected separately or all together at the same time. Regardless of the particular order of injection and/or combination, it is typically preferred that the injection is at substantially the same site (i.e., within an area of equal or less than 200 cm$^2$, or equal or less than 50 cm$^2$, or equal or less than 10 cm$^2$). Likewise, while it is contemplated that the vector, the cytokine, and the checkpoint inhibitor are injected at the same day, injection may also be staged. For example, the vector may be injected between 1-7, or 7-14, or 14-21 days prior to injection of the cytokine and/or the checkpoint inhibitor. Such coordinated and subcutaneous/subdermal administration is thought to increase an immune response (as compared to i.v. administration) against the cancer associated epitope, the cancer specific epitope, or neoepitope by enabling dendritic cell and CD4+/CD8+ cell interactions in or near the draining lymph nodes. Indeed, it is contemplated that by localized subcutaneous/subdermal administration, a sustained immune stimulation is achieved by expression of the cancer associated epitope, the cancer specific epitope, or neoepitope in dendritic cells that are present in higher quantities in and near the skin. Such targeted administration is still further boosted by co-administration of an immune stimulating cytokine (e.g., IL-15, IL-15 superagonist, IL-2, etc.) to the same or near the same site and further co-administration of a checkpoint inhibitor (e.g., ipilimumab). While the immune stimulating cytokines typically activate dendritic cells, T cells, and NK cells and as such provide a stimulating environment, checkpoint inhibitors will significantly reduce inhibitory signals that could otherwise reduce activation of dendritic cells, T cells, and NK cells (or that could even lead to immune tolerance or anergic T cells). Viewed from a different perspective, contemplated compositions and methods will produce an immune reaction against specific antigens that is further amplified by local (and contemporaneous) co-administration of immune stimulating cytokines and checkpoint inhibitors.

In addition, and typically preceding or following (by at least 1 day, or by at least two days, or by at least 4 days, or by at least 7 days, or by at least 2 weeks) the co-administration of the vector, the immune stimulating cytokine, and the checkpoint inhibitor, additional treatment modalities can be implemented to counteract immune suppression and/or to further stimulate an immune response against the cancer specific epitope, or neoepitope. For example, in one contemplated aspect of the inventive subject matter, the patient may receive low dose metronomic chemotherapy and/or radiation therapy, which is thought to not only trigger an antigen cascade from dying tumor cells, but also to subject remaining tumor cells to significant stress, resulting in an up-regulation of various stress related proteins, and especially NKG2D ligands. Consequently, such low dose metronomic chemotherapy and/or radiation therapy is thought to increase the number of tumor antigens in the circulation, which in turn subjects the tumor cell to additional attack by the immune system. Moreover, expression of various stress related proteins, and especially NKG2D ligands, will trigger innate cytotoxicity of the patient's NK cells. As the chemotherapy is typically low dose and metronomic, the chemotherapy will not adversely affect the NK cell population. Due to the prolonged administration of chemotherapy, the NK cell stimulating effect and antigen cascade is thought to be persistent, which further stimulates and broadens an immune reaction against the tumor.

Of course, it should be noted that NK cell therapy may be implemented, typically within 12-24 hours after first chemotherapy administration and/or radiation, to maximize the effect of stress related proteins. Indeed, where tumor cells express NKG2D ligands, activated NK cells will readily exert their cytotoxic effect, which in turn further increases the antigen cascade.

In addition, where antibodies are available against the cancer associated epitope, the cancer specific epitope, or the neoepitope, antibodies (synthetic, recombinant, or isolated) may be provided to the patient to so 'tag' tumor cells, which will in turn be effectors or further cell mediated (and especially NK cell/T cell) killing. Alternatively, or additionally, it should be appreciated that high affinity NK cells, preferably with the antibodies bound to the CD16 protein, can be administered to trigger NK cell mediated antigen-specific cell killing.

Where desired, it is also contemplated that the treatment can be further supported by administration of one or more compounds that reduce activity of Tregs (T regulatory cells), MDSCs (myeloid derived suppressor cells), and/or M2 macrophages. Most typically, such administration will be subsequent to the co-administration of the vector, the cytokine, and the checkpoint inhibitor. In some aspects, the compounds that reduce activity of Tregs, MDSCs, and/or M2 macrophages will be administered at least one day, or at least two days, or at least four days, or at least seven days, or at least two weeks after the co-administration. Such compounds are believed to reduce inhibitory effects by the inhibitory cells in the tumor microenvironment. For example, suitable compounds especially include IL-15 and IL-15 superagonists as these compounds not only up-regulate NK cells, but also down-regulate MDSCs and Tregs. Additionally, or alternatively, gemcitabine or a phosphodiesterase-5 (PDE5) inhibitor may be provided to down-regulate MDSCs and Tregs, preferably in a low-dose and metronomic fashion.

To stimulate T cell activation and proliferation, low dose chemotherapy may also be provided using cyclophosphamide or 5-fluorouracil. These drugs have been shown to activate CD8+ T cells when administered at low doses, and particularly when given in a metronomic fashion. Most typically, such low dose chemotherapy will commence upon or after (e.g., at least 2 days, at least 4 days, at least 7 days, or at least 2 weeks) subcutaneous or subdermal co-administration of the vector, the cytokine, and the checkpoint inhibitor. Thus, it should be appreciated that upon co-administration, an immune response may be extended and amplified (by reduction of immune suppression and stimulation of immune response) to so lead to a substantial stimulation of development of memory T-cells against cancer associated epitopes, cancer specific epitopes, and/or neoepitopes, which in turn will lead to a durable or persistent immune response against such antigens. Such benefits may be further enhanced by (preferably sequential) administration of low-dose chemotherapy and/or radiation, NK cell based therapies, compounds that reduce Tregs, M2 macrophage and MDSCs or increase T cell activity as described above.

For example, contemplated methods may include co-administration of a vector with a recombinant nucleic acid that encodes the at least one of the cancer associated epitope, the cancer specific epitope, and the neoepitope; an immune stimulating cytokine; and (3) a checkpoint inhibitor. Co-administration may then be followed by at least one of low-dose chemotherapy and/or radiation, NK cell based therapies, compounds that reduce Tregs, M2 macrophage and MDSCs or increase T cell activity, or at least two of low-dose chemotherapy and/or radiation, NK cell based therapies, compounds that reduce Tregs, M2 macrophage and MDSCs or increase T cell activity, or low-dose chemotherapy and/or radiation, NK cell based therapies, and compounds that reduce Tregs, M2 macrophage and MDSCs or increase T cell activity. As will be readily appreciated, the use and sequence of low-dose chemotherapy and/or radiation, NK cell based therapies, and/or compounds that reduce Tregs, M2 macrophage and MDSCs or increase T cell activity will depend on various factors, and especially on the treatment progress (e.g., as determined by tumor size, presence and numbers of metastases, etc.) and immune status (e.g., as determined by fraction of activated T cells and memory T and NK cells, antibody titer, etc.).

Moreover, it should be appreciated that the contemplated treatments and methods may be performed iteratively upon assessment of the tumor/metastatic burden. Such second and subsequent treatments may be identical, or various. For example, the choice of the cancer associated epitope, cancer specific epitope, and/or neoepitope may be different where the initial choice led to eradication of one clonal subpopulation but not to eradication of another clonal subpopulation. Likewise, low dose chemotherapy and/or radiation may be omitted where an immune suppression is a hallmark of remaining tumors. Viewed from a different perspective, immune therapy of cancers and memory T cell formation against various cancer antigens can be enhanced by triggering an immune response that is concurrently amplified by administration of immune stimulating cytokines and checkpoint inhibitors, and subsequently boosted by various modalities that up-regulate an immune response and down-regulate one or more suppressive mechanisms. Moreover, it should be noted that by subcutaneous or subdermal injection immunogenic peptides are administered to a site that is rich in dendritic cells and other immune competent cells suitable for antigen presentation.

With respect to the vector, it is generally preferred that the vector is an expression vector from which the cancer associated epitope, the cancer specific epitope, and/or the neoepitope are expressed. To that end, the vector will comprise a recombinant nucleic acid sequence portion that encodes the cancer associated epitope, the cancer specific epitope, and/or the neoepitope, preferably such that the neoepitope is directed to MHC-I and/or MHC-II presentation pathways and MHC sub-type(s) for which the neoepitope is known to have high affinity. Such targeted and rational-based presentation is thought to produce a more robust immune response, which may be further augmented by co-expression of one or more co-stimulatory molecules. Of course, it should be appreciated that all manners of delivery of such recombinant nucleic acid(s) are deemed suitable and that the recombinant nucleic acid(s) may be formulated as a DNA vaccine, as a recombinant viral genome, or a DNA or RNA deliverable in a transfection composition. Therefore, it is noted that all expression systems known in the art are deemed suitable for use herein (e.g., bacterial expression systems, yeast expression systems, 'naked' DNA and RNA expression systems).

However, it is especially preferred to use viruses already established in gene therapy, including adenoviruses, adeno-associated viruses, alphaviruses, herpes viruses, lentiviruses, etc. Thus, among other appropriate choices, adenoviruses are particularly preferred. Still further, it is generally preferred that the virus is a replication deficient and non-immunogenic virus, which is typically accomplished by targeted deletion of selected viral proteins (e.g., E1, E3 proteins). Such desirable properties may be further enhanced by deleting the E2b gene function, and high titers of such recombinant viruses can be achieved using genetically modified human 293 cells as has been recently reported (e.g., *J Virol* 1998 February; 72(2): 926-933; WO 2016/172249). Most typically, expression of the recombinant genes is driven from constitutively active regulatory sequences. However, in other aspects of the inventive subject matter, the regulatory sequences may be inducible, preferably in a selective manner using one or more regulatory signals endogenous to the cancerous tissue or synthetic inducers. In most cases, it is further preferred that the transcript will includes an IRES (internal ribosome entry site) or a 2A sequence (cleavable 2A-like peptide sequence) to again allow for coordinated expression of multiple proteins. Of course, it should be appreciated that the delivery of the cancer associated antigen, cancer specific antigen, or neoepitope need not be performed using a viral vector, but may also be performed using 'naked DNA' or even performed by administration of the peptide or fragments thereof. In such case, association with a carrier and adjuvant is typically preferred.

With respect to the integration of sequence portions that encode the cancer associated epitope, the cancer specific epitope, and/or the neoepitope it should be noted that the antigens may be arranged in numerous manners, and that a transcription or translation unit may have concatemeric arrangement of multiple antigens, typically separated by short linkers (e.g., flexible linkers having between 4 and 20 amino acids), which may further include protease cleavage sites. Such concatemers may include between 1 and 20 antigens (typically limited by size of recombinant nucleic acid that can be delivered via a virus), and it should be noted that the concatemers may be identical for delivery to the MHC-I and MHC-II complex, or different. Therefore, and as noted below, it should be appreciated that various peptides can be routed to specific cellular compartments to so achieve preferential or even specific presentation via MHC-I and/or MHC-II. Viewed from another perspective, it should be recognized that the cancer associated epitope, the cancer specific epitope, and/or the neoepitope may be presented via both presentation pathways, or selectively to one or another pathway at the same time or in subsequent rounds of treatment.

With respect to the 'payload' of the genetically modified virus it is contemplated that expression of more than one antigen is preferred, for example two, three, four, five, and even more, which can be accomplished using multiple distinct modified viruses, or a virus having more than one antigen sequence (e.g., as concatemeric or chimeric sequence). While not limiting to the inventive subject matter, it is generally preferred that antigen sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the antigens can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate. With respect to further suitable configurations and expression cassettes reference is made to co-pending U.S. provisional applications with the Ser. No. 62/302,168, filed Mar. 2, 2016, and the Ser. No. 62/314,366, filed Mar. 28, 2016, incorporated by reference herein.

It should be further appreciated that the antigen sequences (e.g., expressed as single neoepitope or as polytope) may be configured and directed to one or both MHC presentation pathways using suitable sequence elements. With respect to routing the so expressed antigens to the desired MHC-system, it is noted that the MHC-I presented peptides will typically arise from the cytoplasm via proteasome processing and delivery through the endoplasmatic reticulum. Thus, expression of the antigens intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane. Thus, expression of the antigens intended for MHC-II presentation will generally be directed to the endosomal and lysosomal compartment as is also discussed in more detail below.

In most preferred aspects, signal peptides may be used for trafficking the antigens to the endosomal and lysosomal compartment (and with directing the antigen presentation towards MHC-II), or for retention in the cytoplasmic space (and with directing the antigen presentation towards MHC-I). For example, where the peptide is to be exported to the endosomal and lysosomal compartment, targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531).

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

Additionally, it is contemplated that the viral delivery vehicle also encodes at least one, more typically at least two, even more typically at least three, and most typically at least four co-stimulatory molecules to enhance the interaction between the infected dendritic cells and T-cells. For example, suitable co-stimulatory molecules include ICAM-1 (CD54), ICOS-L, and LFA-3 (CD58), especially in combination with B7.1 (CD80) and/or B7.2 (CD86). Further contemplated co-stimulatory molecules include 4-1BBL, CD30L, CD40, CD40L, CD48, CD70, CD112, CD155, GITRL, OX40L, and TL1A. In preferred aspects, the co-stimulatory molecules may be arranged as a combination of four, five, or even more co-stimulatory molecules. For example, a combination of four will include B7.1, B7.2, LFA-1, and ICAM-1, which may be further combined with one or more peptides targeting the CTLA-4 receptor. In such combination of 4 molecules, targeting will not only improve presentation to CD4+ and CD8+ but also stimulate B-cells, improve cell-to-cell adhesion. Moreover, it should be appreciated that expression of the co-stimulatory molecules will preferably be coordinated such that the antigens are presented along with one or more co-stimulatory molecules. Thus, it is typically contemplated that the co-stimulatory molecules are produced from a single transcript, for example, using an internal ribosome entry site or 2A sequence, or from multiple transcripts.

Likewise, it is contemplated that the viral vector will further include a sequence portion that encodes one or more peptide ligands that bind to a checkpoint receptor. Most typically, binding will inhibit or at least reduce signaling via the receptor, and particularly contemplated receptors include CTLA-4 (especially for CD8+ cells) PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented along with one or more peptide molecules. Similarly, contemplated vectors may further include a sequence portion that encodes the immune stimulatory cytokine (e.g., IL-2, IL-7, IL-12, IL-15, or a IL-15 superagonist (e.g., IL15N72D), IL-15 superagonist/IL-15RaSushi-Fc fusion complex (e.g., ALT803), etc.). Thus, it is typically contemplated that the peptide molecules are produced from a single transcript, for example, using an internal ribosome entry site or 2A sequence, or from multiple transcripts. In such event, it should be appreciated that the administration of the vector provides the antigens, the checkpoint inhibitor, and/or the immune stimulating cytokine (which then does/do not need to be injected separately).

With respect to the cancer associated epitope, the cancer specific epitope, and the neoepitope it should be noted that all such antigens are suitable for use herein. For example, suitable cancer associated antigens include brachyury, CEACAM, MUC-1, CYPB1, etc. while suitable cancer-specific antigen include PSA, PSMA, brachyury, Her2/neu, etc. With respect to neoepitopes, it is generally preferred that such neoepitopes are patient and tumor specific. As such, high-throughput genome sequencing allows for rapid and specific identification of patient specific neoepitopes where the analysis also considers matched normal tissue of the same patient. Most preferably, suitable cancer associated epitope, cancer specific epitope, and neoepitope will be further filtered using various criteria, and especially expression level (e.g., present in the tumor above a minimum expression level of at least 20% above matched normal control), location (e.g., anchored to cell membrane) and binding affinity to the MHC complex of the patient to ensure proper presentation to the immune system.

It is generally contemplated that the genomic analysis to identify neoepitopes can be performed by any number of analytic methods, however, especially preferred analytic methods include WGS (whole genome sequencing) and exome sequencing of both tumor and matched normal sample. Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers.

Identification of expression level can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, and more typically at least 50% as compared to matched normal, thus ensuring that the epitope is at least potentially 'visible' to the immune system. Thus, it is generally preferred that the omics analysis also includes an analysis of gene expression (transcriptomic analysis) to so help identify the level of expression for the gene with a mutation. Viewed from another perspective, transcriptomic analysis may be suitable (alone or in combination with genomic analysis) to identify and quantify genes having a cancer and patient specific mutation. There are numerous methods of transcriptomic analysis know in the art, and all of the known methods are deemed suitable for use herein. Taken the above into consideration, it should therefore be appreciated that a patient sample comprising DNA and RNA from tumor and matched normal tissue can be used to identify specific mutations and to quantify such mutations.

Thus, it should be appreciated that the adenoviral nucleic acid construct (or nucleic acid construct for other viral delivery) will preferably include a recombinant segment that encodes at least one patient-specific neoepitope, and more typically encode at least two or three more neoepitopes and/or tumor type-specific neoepitopes and/or cancer-associated neoepitopes. Where the number of desirable neoepitopes is larger than the viral capacity for recombinant nucleic acids, multiple and distinct neoepitopes may be delivered via multiple and distinct recombinant viruses.

With respect to contemplated co-administration of the checkpoint inhibitors, it should be appreciated that the systems and methods according to the inventive subject matter will not only allow for specific targeting (e.g., via neoepitopes or tumor associated antigens) and activation of T-cells and NK cells (e.g., via co-expressed co-stimulatory molecules), but also advantageously allow for at least partial reversal of immune suppression (e.g., via check point inhibitors), which is thought to be particularly effective when co-administered to the same or near the same site as the vector. Notably, while conventional administration of checkpoint inhibitors is often performed by intravenous injection (see e.g., prescribing information for ipilimumab, nivolumab), it is generally preferred that the checkpoint inhibitors are co-administered subcutaneously or subdermally. However, in certain aspects, intravenous (co-) administration is also deemed suitable.

Suitable checkpoint inhibitors include agents that inhibit CTLA-4, PD-1, PD-L1, and other signaling components for checkpoint inhibition. For example, anti-CTLA-4 therapy agents for use in the methods presented herein include anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, ipilimumab, tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, and antibodies disclosed in WO 2001/014424, antibodies disclosed in WO 2004/035607, antibodies disclosed in US 2005/0201994, and antibodies disclosed in EP1212422B 1. Additional anti-CTLA-4 antibodies are described in U.S. Pat. Nos. 5,811,097, 5,855,887, 6,051,227, and 6,984,720.

Suitable anti-PD-1 and anti-PD-L1 agents for use herein include anti-PD-1 and anti-PD-L1 antibodies, human anti-PD-1 and anti-PD-L1 and anti-PD-L1 antibodies, mouse anti-PD-1 and anti-PD-L1 antibodies, mammalian anti-PD-1 and anti-PD-L1 antibodies, humanized anti-PD-1 and anti-PD-L1 antibodies, monoclonal anti-PD-1 and anti-PD-L1 antibodies, polyclonal anti-PD-1 and anti-PD-L1 antibodies, chimeric anti-PD-1 and anti-PD-L1 antibodies. In specific embodiments, anti-PD-1 therapy agents include nivolumab, pembrolizumab, pidilizumab, MEDI0680, and combinations thereof. In other embodiments, anti-PD-L1 therapy agents include atezolizumab, BMS-936559, MEDI4736, MSB0010718C, and combinations thereof. Therefore, exemplary checkpoint inhibitors will be selected from the group consisting of ipilimumab, tremelimumab, nivolumab, pembrolizumab, pidilizumab, MEDI0680, atezolizumab, BMS-936559, MEDI4736, MSB0010718C, and combinations thereof.

Other immune-checkpoint inhibitors include lymphocyte activation gene-3 (LAG-3) inhibitors, such as IMP321, a soluble Ig fusion protein (*J. Immunol* 2007; 179:4202-4211). Other immune-checkpoint inhibitors include B7 inhibitors, such as B7-H3 and B7-H4 inhibitors. In particular, the anti-B7-H3 antibody MGA271 (*Clin. Cancer Res.* 2012; Jul. 15 (18) 3834). Also included are TIM3 (T-cell immunoglobulin domain and mucin domain 3) inhibitors (*J. Exp. Med.* 2010; 207:2175-86 and *J. Exp. Med.* 2010; 207:2187-94).

Regardless of the specific type of checkpoint inhibitor is generally contemplated that the checkpoint inhibitor is co-administered with the vector as described herein using dosages and schedules that will effect a reduction or elimination of checkpoint inhibition. Most typically, dosages will be substantially the same as provided in the prescription information, however, modifications will be readily determined by the skilled artisan.

Further activation of T-cells and NK cells may be achieved by (co-)administration of one or more immune stimulating cytokines, and it is generally contemplated that these cytokines may be administered using dosages well known in the art. Moreover, and as already discussed above, it is generally preferred that the immune stimulating cytokines are co-administered to the same or near the same site by subcutaneous or subdermal injection. However, in at least some alternative aspects, the immune stimulating cytokines may also be administered using alternate routes, including intravenous injection or intraperitoneal injection. For example, suitable cytokines include IL-2, IL-7, IL-15, and IL-21 (and all reasonable combinations thereof), and particularly contemplated cytokines include IL-15 analogs and complexes. For example, IL-15 with a N72D amino acid substitution, which may be further complexed or fused with the IL-15Rα-IgG1 Fc (e.g., *Cytokine* 56:804, and *OncoImmunology* 2:e26442). Moreover, one or more TLR ligands and analogs thereof may be administered to amplify calcium signaling, preferably at or near the site of injection of the other components.

For example, IL-15 may be administered at dosages between 0.01 mcg/kg and 5.0 mcg/kg, or between 0.01 mcg/kg and 0.5 mcg/kg, or between 0.1 mcg/kg and 1.0 mcg/kg, or between 0.5 mcg/kg and 5.0 mcg/kg, or between 0.1 mcg/kg and 2.5 mcg/kg. Recombinant IL-15 is well known in the art and can be produced following well established protocols. Similarly, IL-15 superagonists may be administered at dosages between 0.05 mcg/kg and 15 mcg/kg, or between 0.5 mcg/kg and 5 mcg/kg, or between 1 mcg/kg and 10 mcg/kg, or between 2.5 mcg/kg and 15.0 mcg/kg, or between 1 mcg/kg and 10 mcg/kg (see e.g., *Blood* 2015; 126:1957). Such superagonist is available from Altor BioScience as ALT803 or may be recombinantly produced following protocols well known in the art.

Likewise, IL-2 can be administered following standard dosages, for example, as a two-cycle course of high-dose IL-2 administered intravenously (e.g., each course including two 5-day cycles at 600,000 IU/kg/dose administered over 15 minutes q8h, separated by a minimum of 9 days), or in lower dosages subcutaneously or subdermally. IL-2 is well known in the art and is commercially available as PROLEUKIN® (aldesleukin, human recombinant interleukin-2 product, Prometheus Laboratories).

IL-7 may be administered at dosages up to 100 mcg/kg, or up to 70 mcg/kg, or up to 30 mcg/kg. Thus, suitable dosages will typically be between 10-100 mcg/kg, or between 10-50 mcg/kg, or between 20-60 mcg/kg. Recombinant IL-7 is well known in the art and can be produced following well established protocols. Likewise, IL-12 may be administered at relatively low dosages, and suitable dosages will generally be in the range of between 0.25-0.5 mcg/kg, or between 0.5-2.5 mcg/kg, or between 1.0-3.0 mcg/kg, or between 2.0-5.0 mcg/kg. Recombinant IL-12 is well known in the art and can be produced following well established protocols.

With respect to the immune stimulating cytokine and checkpoint inhibitors, it should be noted that co-administration may be performed independently, contemporaneously or in individual and separately timed administration, and co-administration is most typically performed together with the administration of the vector within the same day, or within 1-3 days, or within 3-5 days, or within 1-7 days, or within 7-14 days. Moreover, it should be appreciated that the immune stimulating cytokine and/or the checkpoint inhibitor may be encoded in the vector and may be expressed from the vector together with the cancer associated epitope, the cancer specific epitope, and/or the neoepitope, typically as a viral expression vector construct. Therefore, co-administration may be effected by co-expression of the cancer associated epitope, the cancer specific epitope, and/or the neoepitope together with the immune stimulating cytokine and/or the checkpoint inhibitor. Regardless of the manner of delivery, co-administration will be under a protocol such that the vector, the cytokine, and the checkpoint inhibitor are present in the patient in measurable quantities at the same time.

To trigger overexpression or transcription of stress signals, it is also contemplated that the patient may be treated with low-dose chemotherapy, preferably in a metronomic fashion, and/or radiation therapy. For example, it is generally preferred that such treatment will be effective to affect at least one of protein expression, cell division, and cell cycle, preferably to induce apoptosis or at least to induce or increase the expression of stress-related genes (and particularly NKG2D ligands). Thus, in one contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic, and cytotoxic drugs are all contemplated herein. However, particularly preferred agents include those identified to interfere or inhibit a component of a pathway that drives growth or development of the tumor. Suitable drugs can be identified using pathway analysis on omics data as described in, for example, WO 2011139345 and WO 2013062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

Where desired, and particularly where neoepitopes of the patient are known, the patient may further receive treatment with a cell-based composition comprising an immune competent cell. For example, particularly suitable immune competent cells include T-cell, optionally having a chimeric antigen receptor, and NK cells, optionally having a high-affinity CD16 or a chimeric antigen receptor. There are numerous NK cells deemed suitable for use herein, and especially contemplated NK cells are described by NantKwest, Inc. (9920 Jefferson Blvd., Culver City, Calif. 90232; see URL: www.nantkwest.com/platform/). Where the cells are genetically modified to have affinity against an epitope, it is especially preferred that such epitopes are neoepitopes as described above. Moreover, the treated cells may also be exposed to antibodies (or fragments thereof) that bind to the tumor neoepitopes. Synthetic antibodies against patient and tumor specific neoepitopes can be prepared as described in WO 2016/172722. Among other benefits, use of antibodies against tumor associated antigens or neoepitopes is thought to be advantageous to directly mark tumor cells and to increase NK-mediated cell killing (particularly where the NK cell has a high affinity CD16 variant).

In view of the above, exemplary contemplated systems and methods will particularly activate dendritic cells by viral delivery of the neoantigens or other cancer-specific or cancer associated antigens. At the same time, or in a subsequent time window (e.g., to allow for suitable expression of the antigens), NK cells and T-cells (especially CD8+ T-cells) are then instructed by the dendritic cells (or other infected antigen presenting cells) and stimulated by appropriate dosages of immune stimulating cytokines, and especially IL-15 and IL-15 analogs, IL-2, etc. to enhance proliferation, maturation, and activity of dendritic cell, NK cell and/or cytotoxic T-cells. Where desired, low-dose chemotherapy can be employed to elicit a stress response in the tumor cells, which will lead to an additional mode (antigen or epitope independent) of NK-cell mediated tumor cell killing. In addition, it should be especially appreciated that by subcutaneous or subdermal route, a longer half life enables draining lymph nodes and thymus to activate these cells and to induce memory T cell formation.

In further exemplary contemplated systems and methods, and with further respect to address immune evasion by the tumor, it should be appreciated that the patient may also be treated with one or more drugs to reduce or eliminate production of macrophage suppressor cells, Tregs, and/or myleoid derived suppressor cells. For example, especially suitable drugs include gemcitabine, sunitinib, nitroaspirin, nab-paclitaxel, ATRA, and selected phosphodiesterase-5 (PDE5) inhibitors. Alternatively, or additionally, certain chemokines may be administered to interfere with chemoattraction of suppressor cells, or one or more pro-inflammatory chemokines may be administered (also preferably subcutaneously or subdermally) to attract additional immune competent cells (e.g., CD4+ T-cells). Moreover, as in most cases a tumor (micro)environment is hypoxic, it is also contemplated that such lack of oxygen may be reversed at least temporarily by use of supplemental oxygen, adenosine receptor inhibitors, and/or avastin (bevacizumab), or be used as specific inducing condition for recombinant genes (e.g., toxic or pro-apoptotic gene products delivered via adenoviral vector) that are under control of hypoxia inducible factors.

In additional exemplary aspects of contemplated methods, an alternative strategy to blocking inhibitory receptors on NK cells with monoclonal antibodies for cancer therapy is the use of agonist antibodies to augment the effector functions of T cells or NK cells. Both strategies comprise the combinations to enhance development of memory T cells in this invention. One example of agonist antibodies or small molecules for increased NK or T cell activity is an antibody against CD137 (also known as 4-1BB and TNFRSF9) which is expressed on both cytotoxic T cells and activated NK cells. Such agonist monoclonal antibodies have been shown to augment antitumor activity in mouse models as well as NK cell activation. Agonist CD137 antibodies have also been shown to enhance the human NK cell-mediated killing of her 2 positive breast tumors and CD20 positive B cell lymphomas, induced by trastuzumab and rituximab ADCC killing respectively. To overcome agonist CD137 antibodies significant toxicities when used at high doses, lower doses might serve to increase antitumor efficacy when combined with other checkpoint blockade therapeutics or with tumor-specific antibodies that induce ADCC. In addition, subcutaneous administration of these agonists together with IL15 and its ligand receptors may enhance NK effects.

The inhibitory receptors on NK cells, such as KIR and NKG2A, may limit their antitumor potential of autologous NK cells when co-stimulatory molecules are administered. Consequently, the inventor contemplates that this limitation may be overcome by the simultaneous or temporal infusion of NK cell lines which are devoid of or have minimal inhibitory receptors (e.g., such as NK92 cells). The first evidence for the clinical benefit of NK cells was reported in 2002 by Velardi and colleagues who observed that patients with AML who received allogeneic NK responded, based on graft versus host immunogenic reaction. Furthermore a recent study has reported severe GVHD in some cancer patients given T cell-depleted allogeneic hematopoietic stem cell transplants infused with allogeneic NK cells pre-activated in vitro with IL-15 and TNFSF9 (also known as 4-1BBL). Although it is not known whether the GVHD was caused directly by the NK cells or the NK cells induced a T cell-mediated GVHD response, the outcome was surprising given that NK cells have not been shown to cause GVHD in previous human clinical trials or in preclinical mouse models. Although the therapeutic efficiency of adoptively transferred IL-2-activated NK cells seems to be limited, recent studies have reported that mouse NK cells activated in vitro with a combination of IL-12, IL-15 and IL-18 survived longer after adoptive cell transfer than naive cells and produced more IFNγ after stimulation. These pre-activated NK cells had better effector functions in vitro, as well as enhanced proliferation, tumor infiltration and tumor control in vivo when tested in mouse models of lymphoma and melanoma.

The inventors also contemplate that agents can be administrated in conjunction with the methods herein that can suppress NK cell effector functions, and exemplary agents include TGFβ, prostaglandin E2, indoleamine 2,3-dioxygenase, adenosine. By combining agents that block these suppressor effects in tandem with NK cell activators (IL-15 or analogs thereof) or infusion of NK92 and its haNK and taNK derivatives, maximum opportunity for tumor killing and generation of memory T cells is contemplated. Further compositions and methods of enhancing NK activity are described in *Nature Reviews Cancer* (2016), Vol. 16, p7-19, incorporated by reference herein. However, that report failed to recognize or suggest that dendritic, NK- and T-cell functions can be enhanced while suppressive mechanisms can be blocked or reversed (e.g., by inhibiting MDSC and Tregs and inhibiting checkpoints as already noted above).

Moreover, the inventor also contemplates various strategies for use herein that couple NK cells to tumor cells or NK cells to T-cells. Among other suitable examples such coupling can be performed using bifunctional antibodies or antibodies (that bind to CD16 of a NK cell of haNK) that recognize tumor or T-cell epitopes. For example, a haNK cell can be loaded with Elotuzumab that binds SLAMF7 (CD319) on multiple myeloma cells. On the other hand, bikes (bispecific killer cell engagers) can be used to couple CD16 on a NK cell with a neoepitope or tumor associated antigen of a cancer cell.

Lastly, it should be appreciated that treatment need not conclude upon administration of the therapeutic modalities described herein, but is typically reiterated using a rebiopsy of residual and/or mutated tumor tissue. In other words, while a first treatment uses omics analysis as guide for targeting a first set of tumor associated antigens and/or neoepitopes, the immune system of the patient may not completely eradicate all tumor cells and/or clones as the tumor cells will invariably change over the course of the treatments. In response, an adaptive and evolving strategy can be employed that identifies new or resistant epitopes for (re)targeting. Such second and subsequent targeting may utilize the same principles as the initial or previous treatment, or may rely at least in part on a modified strategy. For example, adenoviral delivery of nucleic acid encoding a first set of antigens for presentation via MHC-I may be followed by adenoviral delivery of a nucleic acid encoding a first set of antigens for presentation via MHC-II, or a new set of antigens. Likewise, while subcutaneous or subdermal administration is generally preferred, other routes are also expressly contemplated herein (e.g., intravenous, intramuscular, etc.).

The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of stimulating development of memory T-cells against at least one of a cancer associated epitope, a cancer specific epitope, and neoepitope in a patient, the method comprising:
   co-administering by subcutaneous or subdermal injection:
   (1) a vector with a recombinant nucleic acid that encodes the at least one of the cancer associated epitope, the cancer specific epitope, and the neoepitope;
   (2) an IL-15 superagonist;
   (3) a checkpoint inhibitor selected from an anti-PD1 antibody and an anti-PDL1 antibody;
   wherein the step of co-administering is performed under a protocol such that the vector, the cytokine, and the checkpoint inhibitor are present in the patient in measurable quantities at the same time.

2. The method of claim 1 wherein the vector is an adenoviral expression vector.

3. The method of claim 2 further comprising a step of administering a low-dose chemotherapy and/or radiation to stimulate overexpression of the cancer associated epitope, the cancer specific epitope, the neoepitope, and/or a NKG2D ligand.

4. The method of claim 2 further comprising a step of administering a drug that reduces number or function of Tregs, M2 macrophages and/or myeloid derived suppressor cells.

5. The method of claim 4 wherein the drug is gemcitabine, nab-paclitaxel, or a phosphodiesterase-5 (PDES) inhibitor.

6. The method of claim 2 further comprising a step of administering a drug that increases T-cells when given metronomically in low doses.

7. The method of claim 6 wherein the drug is cyclophosphamide or 5-fluorouracil.

8. The method of claim 2 further comprising a step of administering an additional chemokine.

9. The method of claim 2 further comprising a step of administering a cell-based composition comprising an immune competent cell.

10. The method of claim 9 wherein the immune competent cell is a T-cell, optionally having a chimeric antigen receptor, or an NK cell, optionally having a high-affinity CD16 or a chimeric antigen receptor.

11. The method of claim 2 wherein the recombinant nucleic acid further encodes at least one of an additional cytokine, a co-stimulatory molecule, and a checkpoint inhibitor.

12. The method of claim 11 wherein the co-administration of the at least one of the additional cytokine and the checkpoint inhibitor is by expression from the recombinant nucleic acid.

13. The method of claim 2 wherein the adenoviral expression vector is an adenovirus type 5 virus with an E2b gene region deletion.

14. The method of claim 2 wherein the vector, the cytokine, and the checkpoint inhibitor are injected at substantially the same site within one to five days.

15. A method of eliciting a durable immune response against a tumor expressing at least one of a cancer associated epitope, a cancer specific epitope, and neoepitope in a patient, comprising:
   co-administering by subcutaneous or subdermal injection:
   (1) a vector with recombinant nucleic acid that encodes the at least one of the cancer associated epitope, the cancer specific epitope, and the neoepitope;
   (2) an IL-15 superagonist;
   (3) a checkpoint inhibitor selected from an anti-PD1 antibody and an anti-PDL1 antibody;
   wherein the step of co-administering is performed to trigger formation or propagation of memory T-cells in an amount sufficient to produce a persistent immune response against the tumor.

16. The method of claim 15 wherein the adenoviral expression vector particle is an adenovirus type 5 virus with an E2b gene region deletion.

17. The method of claim 16 further comprising at least one of a step of
   (1) administering low-dose chemotherapy and/or radiation under a protocol effective to stimulate overexpression of a cancer associated epitope, a cancer specific epitope, a neoepitope, and/or a NKG2D ligand;
   (2) administering a drug that reduces production of Tregs, M2 macrophage, and/or myeloid derived suppressor cells;

(3) administering a drug that increases T-cells when given metronomically in low doses;
(4) administering a chemokine; and
(5) administering a cell-based composition comprising an immune competent cell.

18. The method of claim 17 further comprising at least two of a step of
   (1) administering low-dose chemotherapy and/or radiation under a protocol effective to stimulate overexpression of a cancer associated epitope, a cancer specific epitope, a neoepitope, and/or a NKG2D ligand;
   (2) administering a drug that reduces production of Tregs, M2 macrophage, and/or myleoid derived suppressor cells;
   (3) administering a drug that increases T-cells when given metronomically in low doses;
   (4) administering a chemokine; and
   (5) administering a cell-based composition comprising an immune competent cell.

19. The method of claim 18 further comprising at least three of a step of
   (1) administering low-dose chemotherapy and/or radiation under a protocol effective to stimulate overexpression of a cancer associated epitope, a cancer specific epitope, a neoepitope, and/or a NKG2D ligand;
   (2) administering a drug that reduces production of Tregs and/or myleoid derived suppressor cells;
   (3) administering a drug that increases T-cells when given metronomically in low doses;
   (4) administering a chemokine; and
   (5) administering a cell-based composition comprising an immune competent cell.

20. The method of claim 16 wherein the vector, the cytokine, and the checkpoint inhibitor are injected at substantially the same site within 1-21 days.

* * * * *